United States Patent [19]
Kitchin et al.

[11] Patent Number: 4,520,820
[45] Date of Patent: Jun. 4, 1985

[54] AUTOMATIC TOURNIQUET WITH IMPROVED PRESSURE RESOLUTION

[75] Inventors: Dwight W. Kitchin; Michael R. Manes, both of Littleton, Colo.

[73] Assignee: Aspen Laboratories, Inc., Englewood, Colo.

[21] Appl. No.: 485,548

[22] Filed: Apr. 15, 1983

[51] Int. Cl.³ .............................................. A61B 17/12
[52] U.S. Cl. ..................................................... 128/327
[58] Field of Search ................ 128/327, 678, 682, 686

[56] References Cited
FOREIGN PATENT DOCUMENTS
8300995 3/1983 Int'l Pat. Institute .............. 128/327

Primary Examiner—Michael H. Thaler
Attorney, Agent, or Firm—Paul David Schoenle

[57] ABSTRACT

An automatic tourniquet including a mechanism for inflating and deflating a cuff, a pressure sensing mechanism, and a mechanism for displaying the pressure. The pressure sensing mechanism includes a pressure transducer producing a pair of digital signals, and a mechanism for adjusting the signals so that the pressures at which the transitions between the digital quanta occur for one signal are different from the pressures at which the transitions occur for the other signal. The mechanism for adjusting includes a mechanism for setting the signals to be equal at a selected pressure, and a mechanism for offsetting the signals from each other by a voltage corresponding to one-half a digital quantum. The offset signals are summed by a microprocessor to produce a display with twice the resolution of the individual signals.

15 Claims, 13 Drawing Figures

AUTO-ZERO

AUTOMATIC TOURNIQUET WITH IMPROVED PRESSURE RESOLUTION

BACKGROUND OF THE INVENTION

1. Field of the Invention

The invention in general relates to the field of medical pneumatic tourniquets, and more particularly to a tourniquet which is automatically controlled to maintain the desired tourniquet pressure.

2. Description of the Prior Art

Tourniquets are used in medicine to stop the flow of blood into a patient's limb. A typical use is to provide a "bloodless field" in which surgical procedures may be performed on a limb, without the field being obscured by blood, and without loss of blood to the patient. Tourniquets are also used in emergency procedures to prevent loss of blood when a limb is damaged or in any other instance where it is desired to prevent blood flow to a limb.

Tourniquets conventionally consist of an inflatable cuff which is wrappd around the patient's limb, and a source of compressed gas for inflating the cuff. In order to successfully stop the flow of blood the pressure in the cuff must be above the highest level of the patient's blood pressure. However, it should not be so high that it damages the tissue of the limb. Thus in conventional tourniquets a pressure gauge for measuring the cuff pressure, and a pressure regulating mechanism is provided.

Up until very recently, conventional pneumatic tourniquets have been manually controlled mechanical devices. That is, a mechanical mechanism visually indicated the pressure and the pressure was adjusted by an attendant using a mechanical valve.

Recently, an automatic tourniquet for medical use has been created by Dr. James A. McEwen. This tourniquet is described in U.S. patent application Ser. No. 193,145 filed Oct. 2, 1980. An improved automatic tourniquet is described in U.S. patent application Ser. No. 337,152 filed Jan. 5, 1982, also by Dr. James McEwen. In these automatic tourniquets, the pressure in the cuff is continuously sensed and adjusted and displayed by a microprocessor. In addition, the microprocessor activates alarms if a dangerous pressure condition is sensed. It has been found that such automatic tourniquet systems not only are much more convenient in the operating room setting, but also significantly reduce the incidence of limb paralysis, nerve damage and other injuries attributable to tourniquets.

The preferred pressure measuring unit for hospital tourniquet systems is the millimeter of mercury (mmHg). The maximum tourniquet pressures are in the range 400 to 500 mmHg. Thus a preferred scale for measurement of pressure is from 0 to about 500 mmHg. In order to read such a scale in single units of mmHg, a digital system having processing capabilities for 9 bits of information is preferable, since an 8 bit system is capable of expressing only $2^8 = 256$ unique integers, while a 9 bit system is capable of handling $2^9 = 512$. At the same time, it has developed that the microprocessor industry has standardized components available in an 8 bit mode.

SUMMARY OF THE INVENTION

It is an object of the present invention to provide a pneumatic tourniquet in which a pressure scale of more than 500 mmHg in 1 mmHg steps is provided with standard 8 bit technology.

It is also an object of the invention to provide a pneumatic tourniquet system having a pressure resolution greater than the resolution of its analog to digital converter, memory, and similar digital components.

It is again an object of the invention to provide one or more of the above objects in a tourniquet system which uses a minimal number of components, which are all standard electronic components.

The invention provides a pneumatic tourniquet comprising a means for inflating and deflating a cuff, a pressure sensing means for sensing the pressure in the cuff and for producing a plurality of digital signals, each signal representative of said pressure and each signal having a pessure to digital signal scale such that the pressure at which the transitions between digital quanta occur are different for each signal, and display means responsive to the plurality of signals for producing a pressure display having greater resolution than each of the digital signals. Preferably each of the digital signals is an 8 bit signal, and the pressure display has a resolution corresponding to 9 bits for converting the analog signals to digital signals. Preferably the analog pressure signals are electrical voltage signals and the means for producing the signals comprises a means for adjustng the relative voltage levels of the signals. Preferably the means for adjusting the voltage includes a means for adjusting the voltages to be equal at a selected pressure, and a means for offsetting the voltage levels of the two signals with respect to each other. Preferably the selected pressure at which the voltage is adjusted corresponds to substantially the one-half full scale pressure of the pressure transducer, and the voltage signals are offset from one another in an amount corresponding to substantially one-half of a digital quantum. Preferably the means for producing a pressure display includes a means responsive to the voltage signals for producing an output signal representative of the combination of the two signals. Since the signals are offset by a voltage corresponding to about one-half a digital quantum, as the pressure and voltage changes over one digital quantum the combination signal will change twice. This in effect provides twice the resolution than is available in either of the individual digital signals.

The invention in effect simplifies and reduces the cost of the analog to digital conversion system significantly. In addition, the invention leads to an analog system in which system errors and electrical drift can more effectively be compensated for. Numerous other aspects, features, objects and advantages of the invention will now become apparent from the following detailed description when read in conjunction with the accompanying drawings, in which:

DESCRIPTION OF THE PREFERRED EMBODIMENT

Figure 1:
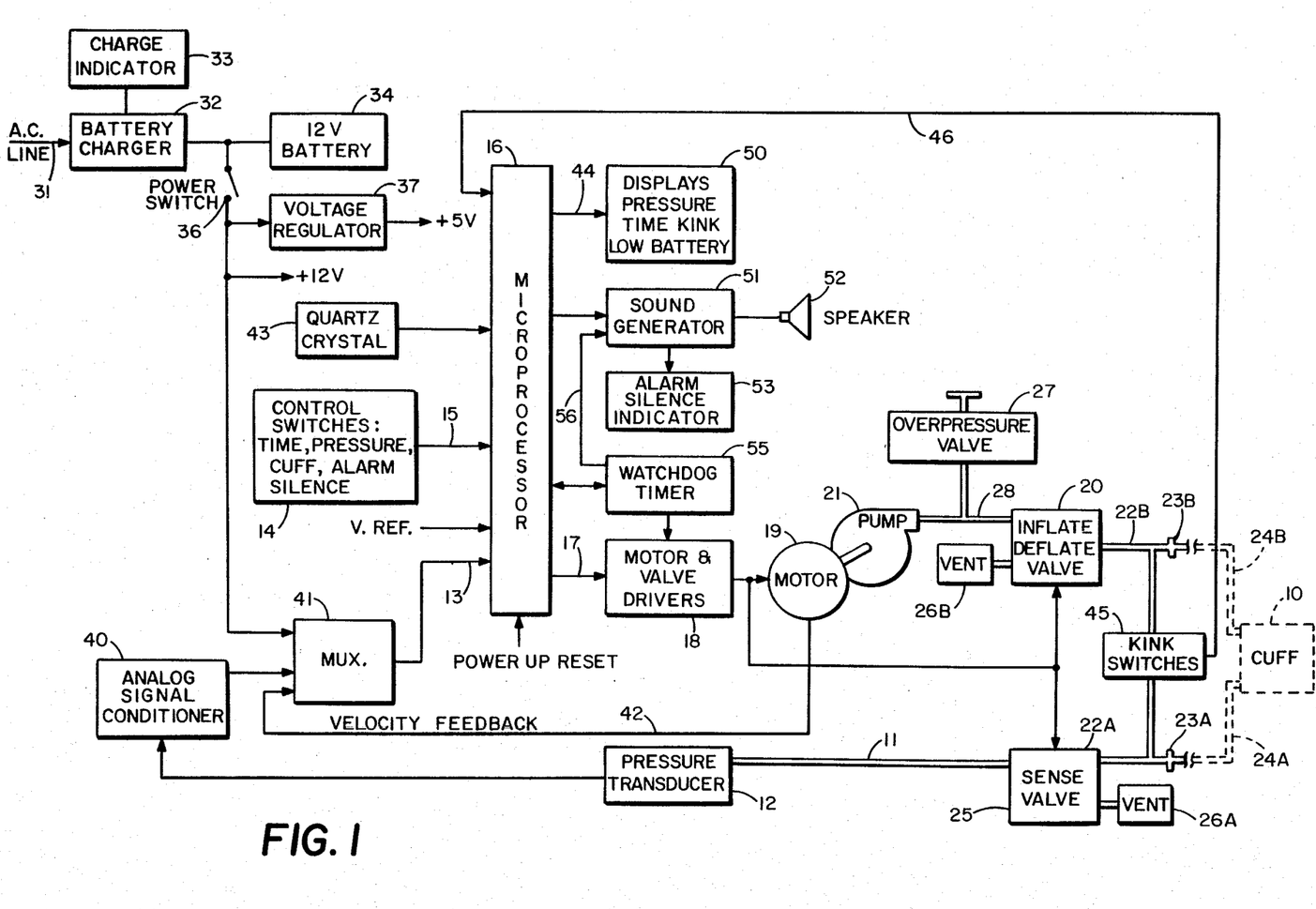
FIG. 1 is a block diagrammatic illustration of the invention showing the various functional elements of the preferred embodiment.

FIG. 1 shows a block diagram of an automatic tourniquet. According to the invention, a pressure sensing means including pressure transducer 12, analog signal conditioner 40, and multiplexer 41 produce a pair of signals which are fed into the microprocessor 16 on line 13. The signals are quantized in an analog-to-digital converter within the microprocessor 16. Within the analog signal conditioner 40, the level of the signals are offset from one another so that the pressures at which the transistions between the digital quanta occur in the microprocessor are different for each of the signals. A display means, which includes a memory and signal processing circuitry within the microprocessor 16 and displays 50, produces a pressure display having twice the resolution than either of the quantized pressure signals. In the preferred embodiment there are two analog signals, which are shown as P— and P+ in FIG. 2a. These signals are fed into microprocessor 16 at its 5 and 6 inputs via multiplexer 68. The two signals, which are labeled AN1 and AN0 in the microprocessor 16, are quantized and summed in a manner which shall be discussed below, to produce output signals on pins No. 20 through No. 23 of the microprocessor 16. The output signals drive pressure display LEDs I4 through I7.

Turning now to a more complete description of the preferred embodiment of the invention, an inflatable cuff 10 is shown connected via tubing 24A and 24B to the automatic tourniquet at couplings 23A and 23B. Coupling 23A is connected via valve 25 and pressure line 11 to a pressure transducer 12. The cuff is shown in dotted line because it may be sold separately from the tourniquet. A signal representing the pressure measured by pressure transducer 12 is applied via electrical line 13 to microprocessor 16. One of control switches 14 is used to apply a signal on line 15 to microprocessor 16 to set a selected pressure. Microprocessor 16 is programmed to calculate a cuff pressure adjustment proportional to the magnitude of the difference between the sensed pressure and the selected pressure, and produces an output signal on line 17 which indicates the cuff pressure adjustment. Electronic motor and valve drive circuitry 18 is responsive to the signal on line 17 to produce a drive signal which is applied to motor 19 and inflate-deflate valve 20. The motor 19 drives a pump 21 for the time determined by microprocessor 16 to inflate cuff 10 through line 24B if the sensed pressure is below the selected pressure. Valve 20 vents the pressure in cuff 10 via vent 23 for the time determined by microprocessor 16 if the sensed pressure is above the selected pressure.

Power is applied to the tourniquet through AC line 31 or via 12volt battery 34. A battery charger 32 maintains battery 34 in a charged condition while the AC power is available. A charge indicator 33 indicates that the battery 34 is being charged. Power is applied to the tourniquet systems through switch 36. A voltage regulator 37 provides a 5-volt regulated voltage which is used to power the portions of the digital circuit requiring a positive 5-volt voltage. The 12-volt voltage output is also provided for portions of the circuitry such as the valves, pumps, and pressure transducer which require a 12-volt power source. The signal from pressure transducer 12 is applied to an analog signal conditioner 40, as mentioned above, and the signal from the analog signal conditioner 40 is applied to an analog multiplexer 41 which gates the signal into the microprocessor 16 at the proper time in which the microprocessor will recognize it. A sample of the motor voltage is also applied to the multiplexer 41 via line 42 and gated into the microprocessor via line 13 at the appropriate time. The timing for the microprocessor 16 is provided by quartz crystal 43. Differential pressure switches 45 are connected between lines 22A and 22B. If any obstruction occurs between lines 22A and 22B, switches 45 apply a signal to microprocessor 16 through line 46.

The microprocessor 16 utilizes the information and the signals applied to it to control the tourniquet and to provide information to the operator. Signals are applied from microprocessor 16 to the displays 15 to indicate the selected and sensed pressure, the time the tourniquet has been on, the selected alarm time setting, whether there is an obstruction (kink), and the condition of the battery 34. Signals are also applied to sound generator 51, which intreprets the signals to generate a predetermined sound at speaker 52 indicitive of the particular alarm condition. The alarm may be silenced if desired via one of control switches 14, in which case a signal is passed via microprocessor 16 and sound generator 15 to alarm silence indicator 53 to indicate that the alarm has been silenced. Timing signals are passed between microprocessor 16 and a watchdog timer 55, which permits the watchdog timer to detect any timing errors which would indicate malfunction of the microprocessor 16. If a timing error is observed, watchdog timer 55 applies a signal to motor and valve drivers circuitry 18 which shuts off the motor 19 and closes the valve 20 thereby isolating the cuff from the presurizing and depressurizing mechanism, and via line 56 causes an audible alarm to be sounded.

Sense valve 25 is connected between cuff 10 and pressure transducer 12. The sense valve 25 connects the pressure transducer 12 to atmosphere through vent 26A during the tourniquet's start-up sequence in order to correct the pressure transducer's zero offset. Overpressure valve 27 is connected to the line 28 between pump 21 and inflate-deflate valve 20. This is a manually adjustable valve which limits the maximum pressure delivered to the cuff in the event that all their safeguards in the motor/pump control system fail.

Figure 2A:
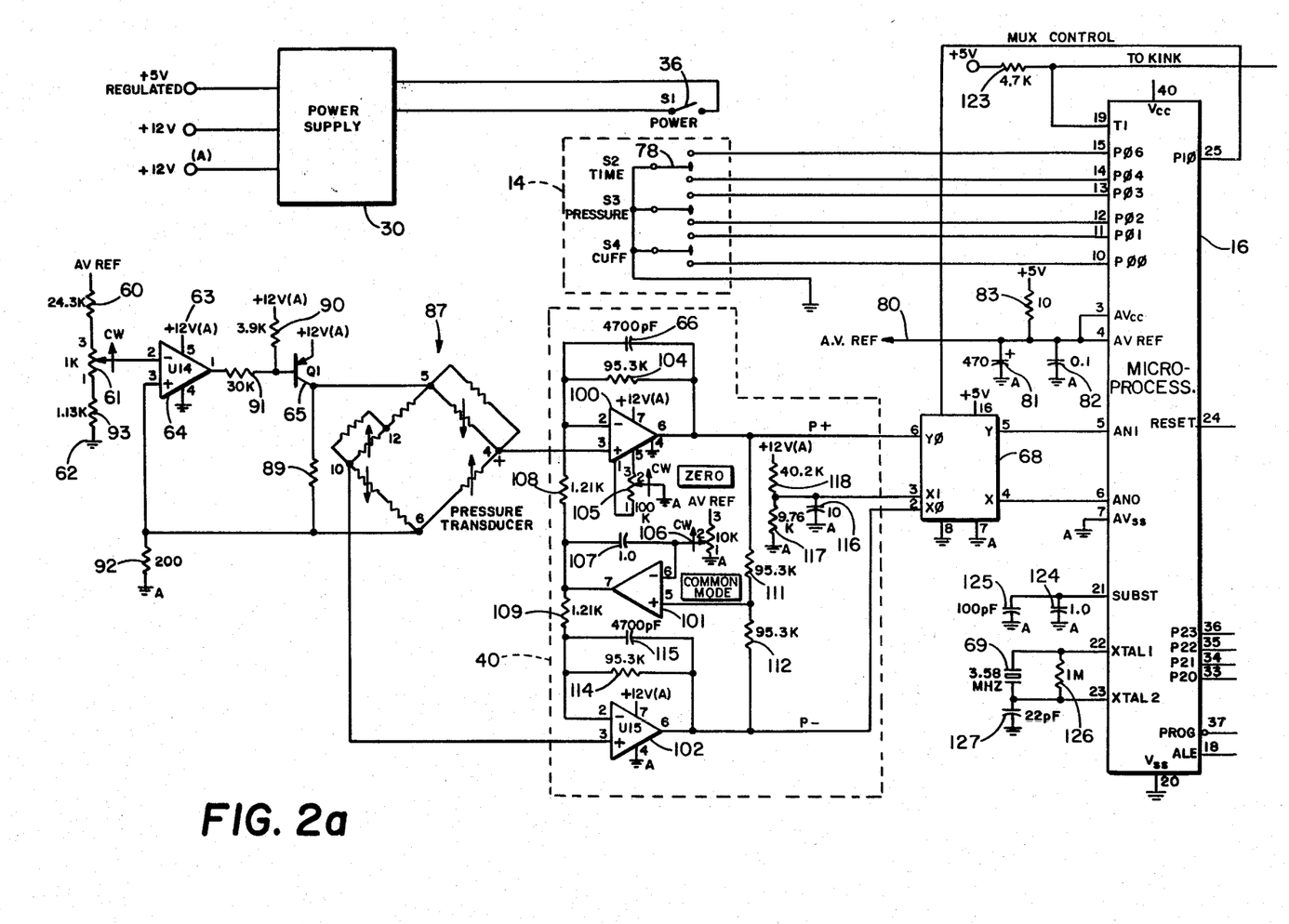
FIG. 2a is the left half and FIG. 2b is the right half of a diagram showing the electronic circuitry in the preferred embodiment of the invention.
Figure 2B:
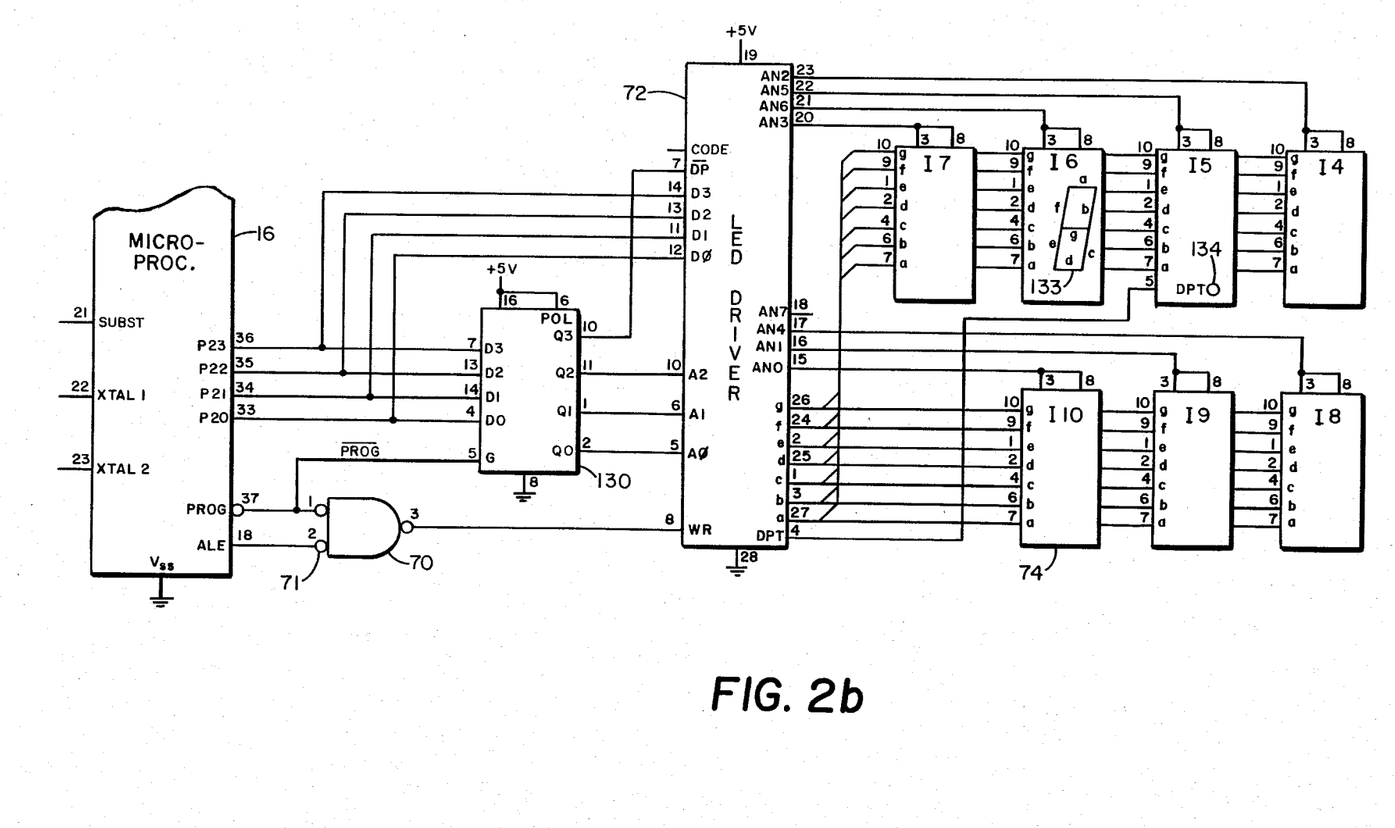

The detailed electronic circuitry of the invention is shown in FIGS. 2a and 2b. These figures do not include all the electronic circuitry of the tourniquet shown in FIG. 1, but only those portions which are relevant to the invention claimed herein. Microprocessor 16 is shown at the right of FIG. 2a and at the left of FIG. 2b in order to provide continuity between the two Figs. If the two Figs. are placed with the microprocessor 16 in each of the Figs. superimposed, the connections between the circuits of the two Figs. will be evident.

The electrical components in FIGS. 2a, and 2b are shown by their common electrical symbols, when such symbols exist. Reviewing these symbols, starting from the left in FIG. 2a and proceeding to the right in FIG. 2b, resistors are shown as at 60, with a notation next to the resistor indicating the value of the resistor, as for example, resistor 60 has the resistance 24.3 kilo-ohms. 61 is a variable resistance for which the resistance increases when turned clockwise. A ground is shown at 62. Both an analog and a digital ground are provided, with the analog ground being shown by an (A) next to the ground. A voltage input is shown by an indicated voltage at the end of a line such as at 63. As will be discussed below, four input voltages are available in the circuit: a positive 12-volt digital indicated by a +12 V, positive 12-volts analog indicated by a +12 V (a), a positive 5-volt regulated supply indicated by a +5 V, and a stable positive 5-volt reference voltage indicated by AVREF. An operational amplifier is shown at 64, with the inverted input indicated by the minus sign and the non-inverted input shown by the plus sign. The numbers located at the point of juncture of lines with the electrical components, such as the 2 and 3 located at the connections to the inverting and non-inverting inputs to operational amplifier 64, indicate the pin numbers of the component to which the line is attached. The component indicated at 65 is a transistor. A capacitor is indicated at 66. Each capacitor has its capacitance value indicated next to it. The rectangle 68 is indicative of an integrated circuit. The particular circuits will be discussed below. At 69 a piezoelectric crystal is shown.

Turning to FIG. 2b, a negative input NAND gate is shown at 70. The small circles such as 71 at an input or output of a device indicates that that input or output is an inverting input or output. The symbols written within the integrated circuits at the point where lines enter or leave the circuit, refer to the signals which are input or output to the circuit at those points. For example, the signal input into microprocessor 16 at line 5 is referred to as the AN1 signal. These signals shall be useful in discussions below regarding the operation of the integrated circuits.

Power to the tourniquet system is supplied by power supply 30, which produces a 5-volt regulated output, and 12-volt outputs for the analog and digital portions of the circuitry. Power is applied to all three outputs when switch 36, located on the front panel of the tourniquet, is closed. Control switches 14, also located on the front panel of the tourniquet, include three single-pole, double-throw, center-off switches such as 78. Switch 78 controls the length of time that the tourniquet may be left on before an alarm is sounded. In the upwards position the switch grounds input 15 to the microprocessor to produce an increase in time setting, while in the lower position switch 78 grounds pin 14 of the microprocessor to produce a decrease in the time setting. Similarly switch S3 may be used to increase or decrease a selected pressure level, and switch S4 may be used to inflate or deflate the cuff.

A fourth output voltage AVREF is produced at 80. This is an approximately 5-volt output voltage which is isolated from the 5-volt regulated voltage by capacitors 81 and 82 and resistor 83. This reference voltage is applied to pins 3 and 4 of the microprocessor and also to other portions of the circuitry as indicated.

The circuitry in the lower left hand portion of FIG. 2a from resistors 60, 61, and 62 through 2 to 1 multiplexer 68 is the circuitry for detecting the cuff pressure and inputing it into the microprocessor. The pressure in the cuff is detected by pressure transducer 87. The pin 5 of transducer 87 is connected to the collector of transistor 65, while pin 6 of the transducer is connected to the collector though resistor 89. The emitter of transistor 65 is connected to the 12-volt analog power supply. The base of transistor 65 is connected to a 12-volt analog power supply through resistor 90 and to the output of operational amplifier 64 through resistor 91. The non-inverting input of operational amplifier 64 is connected to pin 6 of the pressure transducer 87 and to ground through resistor 92. The inverting input to operational amplifier 64 is connected to the output of potentiometer 61. One side of potentiometer 61 is connected to the AVREF voltage through resistor 60, while the other side is connected to the analog ground through resistor 93.

The circuitry 40 between transducer 87 and multiplexer 68 is an analog signal conditioner which adjusts the level of the voltages output from the transducer 87. As will be seen below, this circuitry adjusts the voltage level of the two signals P+ and P− with respect to each other so that the transistions between digital bits in the A to D converter in microprocessor 16 occur at different pressures for the two signals. The positive varying (+) output of transducer 87 (pin 4) is applied to the non-inverting input of operational amplifier 100. The negatively varying output of transducer 87 (pin 10) is applied to the non-inverting input of operational amplifier 102. Capacitor 66 and resistor 104 are connected in parallel across the inverting input and the output of operational amplifier 100. Potentiometer 105 is connected across the 1 and 5 pins of operational amplifier 100. Potentiometer 106 is connected across the AVREF voltage and the analog ground and its output is applied to the inverting input of operational amplifier 101 and to the inverting inputs of operational amplifiers 100 and 102 through capacitor 107 and resistors 108 and 109 respectively. The output of operational amplifier 101 is also connected to the inverting inputs of operational amplifiers 100 and 102 through resistors 108 and 109 respectively. The non-inverting input of operational amplifier 101 is connected to the outputs of operational amplifiers 100 and 102 through resistors 111 and 112 respectively. Resistor 114 and capacitor 115 are connected in parallel across the inverting input and the output of operational amplifier 102. The output of operational amplifier 100 is labeled P+ and is applied to the number 6 pin of multiplexer 68, while the output of operational amplifier 102 is designated P− and is connected to the number 2 pin of the multiplexer. Capacitor 116 and resistor 117 are connected in parallel between the analog ground and the number 3 pin of multiplexer 68. The number 3 pin of multiplexer 68 is also connected to the 12-volt analog power supply through resistor 118. The number 7 pin of the multiplexer is connected to the analog ground while the number 8 pin is connected to the digital ground. The 5-volt regulated power supply is connected to pin 16 of the multiplexer 68. The control of the multiplexer 68 is provided via connection of pin 9 of the multiplexer to output pin 25 of microprocessor 16. The number 5 output of multiplexer 68 is connected to the number 5 input of microprocessor 16 while the number 4 output of multiplexer 68 is connected to the number 6 input of multiplexer 16. The number 19 input of microprocessor 16 is connected to the kink switches (FIG. 2b) and also to the 5-volt power supply via resistor 123. Capacitors 124 and 125 are connected in parallel between the analog ground and pin 21 of the microprocessor. Crystal 69 and resistor 126 are connected in parallel across the 22 and 23 input pins of microprocessor 16. Input 23 is also connected to the digital ground through capacitor 127. Pin 20 of the microprocessor is connected to the digital ground while pin 40 is connected to the 5-volt regulated power supply.

Turning now to the circuit of FIG. 2b, the number 18 output of microprocessor 16 is connected to the number 2 input of negative input NAND gate 70. The inverted number 37 output of microprocessor 16 is connected to the number 1 input of gate 70 and to the number 5 input to latch 130. The numbers 33, 34, 35, and 36 output pins of microprocessor 16 are connected to the numbers 4, 14, 13, and 7 input pins of latch 130 respectively, and also to the number 12, 11, 13, and 14 input terminals of LED driver 72. The number 8 pin of latch 130 is grounded while the number 6 and number 16 pins are connected to the 5-volt voltage source. The number 2, 1, 11, and 10 output pins of latch 130 are connected to the number 5, 6, 10, and 7 input terminals of LED driver 72 respectively. The number 3 output terminal of inverted NAND gate 70 is connected to the number 8 input terminal of LED driver 72. The number 28 pin of LED driver 72 is grounded while the number 19 pin is attached to the +5 voltage source.

The number 20, 21, 22, and 23 outputs of LED driver 72 are each connected to the number 3 and number 8 inputs of LEDs I7, I6, I5, and I4 respectively. The number 15, 16, and 17 outputs of driver 72 are applied to the number 3 and number 8 inputs of LEDs I10, I9, and I8 respectively. The number 18 pin of LED driver 72 is floating. The number 27, 3, 1, 25, 2, 24, and 26 output pins of LED driver 72 are connected to the number 7, 6, 4, 2, 1, 9, and 10 input pins of each of LEDs I4 through I10. The number 4 output pin of driver 72 is connected to the number 5 input of LED I5.

Each of LEDs I4 through I10 is a 7-segment display. One segment of the display illuminates for each of the input signals a through g on the input pins of the LED. The relationship between which of the segments will light and the pins is shown at 133 on LED I6. Each of the LEDs also has a decimal point, which is illuminated when the 5 input is high. This is shown at 134 on LED I5; only this ID has the 5 pin connected to the driver 72. LEDs 4 through 7 comprise the pressure display, while LEDs 8 through 10 comprise the time display.

The various electronic components may be purchased at an electronics supply house. The following are components used in the preferred embodiment. Amplifiers 64 and 101 are an LM358 dual op-amp integrated circuit. Amplifiers 100 and 102 are CA3160 single op-amps. Transistor 65 is an MPS6533. Transducer 87 is a Foxboro series 1800 transducer. Multiplexer 68 is a Motorola MC14551. Crystal 127 is a 3.58 MHZ crystal. Microprocessor 16 is an Intel 8022 single component 8-bit microcomputer with on-chip A/D converter. Negative input NAND gate 70 is actually purchased configured as a CMOS Quad OR gate type 4071. Latch 130 is preferably a 4042. LED driver 72 is an Intersil 8-digit LED driver number ICM7218C. The LEDs are conventional 7-segment LEDs available from many sources. The other components such as the resistors, capacitors, and relay are all standard.

Valves 20 and 25 are preferably Clippard Model EVO-3-12 valves and may be obtained from Clippard Instrument Laboratories, Inc. 7390 Colerain Road, Cincinnati, Ohio. The muffled vents 23 and 26 are models 1507 obtainable from Clippard. Motor 19 is a 12-volt DC motor. Many fluid pumps may be used, although preferably a quiet and highly reliable pump should be used. Kink switches 45 are preferably Fairchild PSF100A-20C differential pressure switches available from Fairchild/Schlumberger, 75 Mall Drive, Commack, N.Y. 11725. Valve 27 is preferably a Clippard CS-30-393 regulator (light spring). The tourniquet cuffs are Inflato-Matic pneumatic tourniquet cuffs which are available from Zimmer, Inc., Warsaw, Ind. 46580.

All of the above components are disclosed only as exemplary embodiments of the components of the invention, and many equivalent components may be substituted for them.

A specification and description is available with the Intel 8022 Microprocessor and any other microprocessor that can be substituted in the invention. Using this description, and the knowledge generally available with respect to the programming of such microprocessors, suitable programs for carrying out the invention can be constructed from the materials disclosed herein. Many such programs are possible. We shall discuss below the preferred embodiment of such a program that has been implemented to carry out the invention.

Figure 3A:
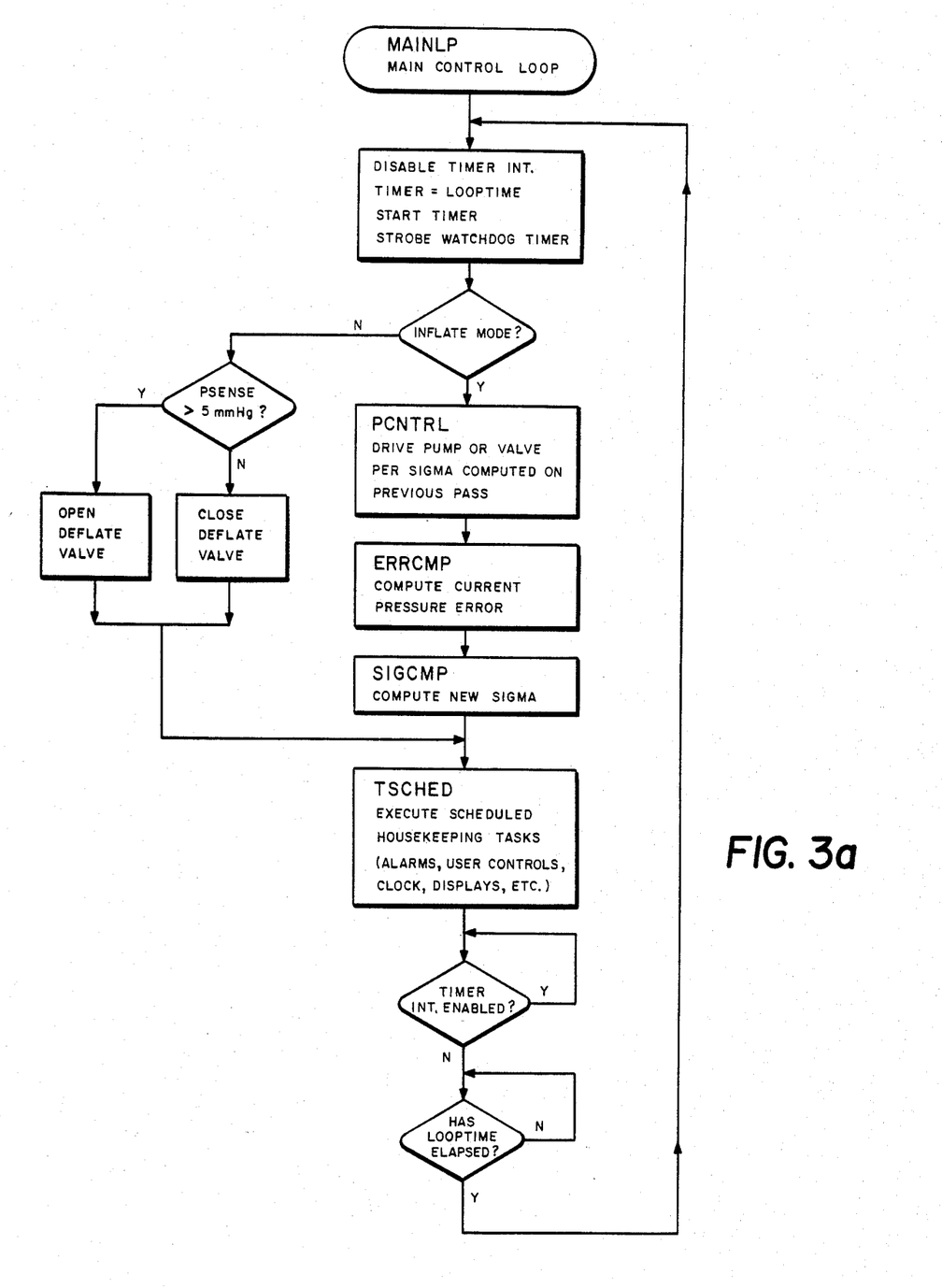
FIGS. 3a through 3f are flow-charts showing the preferred flow of the sequence of operations within the microprocessor according to the invention.

The main microprocessor program loop is shown in FIG. 3a. This program controls the timing of the running of the motor 19 and the opening and closing of valve 20 to control the pressure in cuff 10. The timing of the main loop is controlled by an internal microprocessor timer which causes the loop to repeat with a period $T_L$, of 34 milliseconds as shall be described below. Within the loop, a time $T_{pw}$, is calculated, which is the pulse width time, i.e. the time over which the motor may be on or the valve 20 may be open. On the next loop after which $T_{pw}$ is calculated, the pump 21 or valve 20 is energized from the time $T_0$ to $T_{pw}$. At the time $T_{pw}$ the internal microprocessor timer generates an interrupt to the microprocessor control, and the same time is loaded to finish the loop, i.e. to continue for the time $(T_L - T_{pw})$.

Turning now to a more detailed description of the program, in reference to FIGS. 1, 2a, 2b, and FIG. 3a, the program first resets both the internal microprocessor timer and the watchdog timer. The watchdog timer is set by a strobe signal from the microprocessor which is produced by a sub-program WDTSTB. If the operator has indicated that the cuff is to be deflated, the internal timer is set to $T_L$ and, if the sensed cuff pressure exceeds 5 mmHg, the deflate valve is opened. If the operator has indicated that the cuff should be inflated, the program control passes to the PCNTRL program (see FIG. 3b).

Figure 3B:
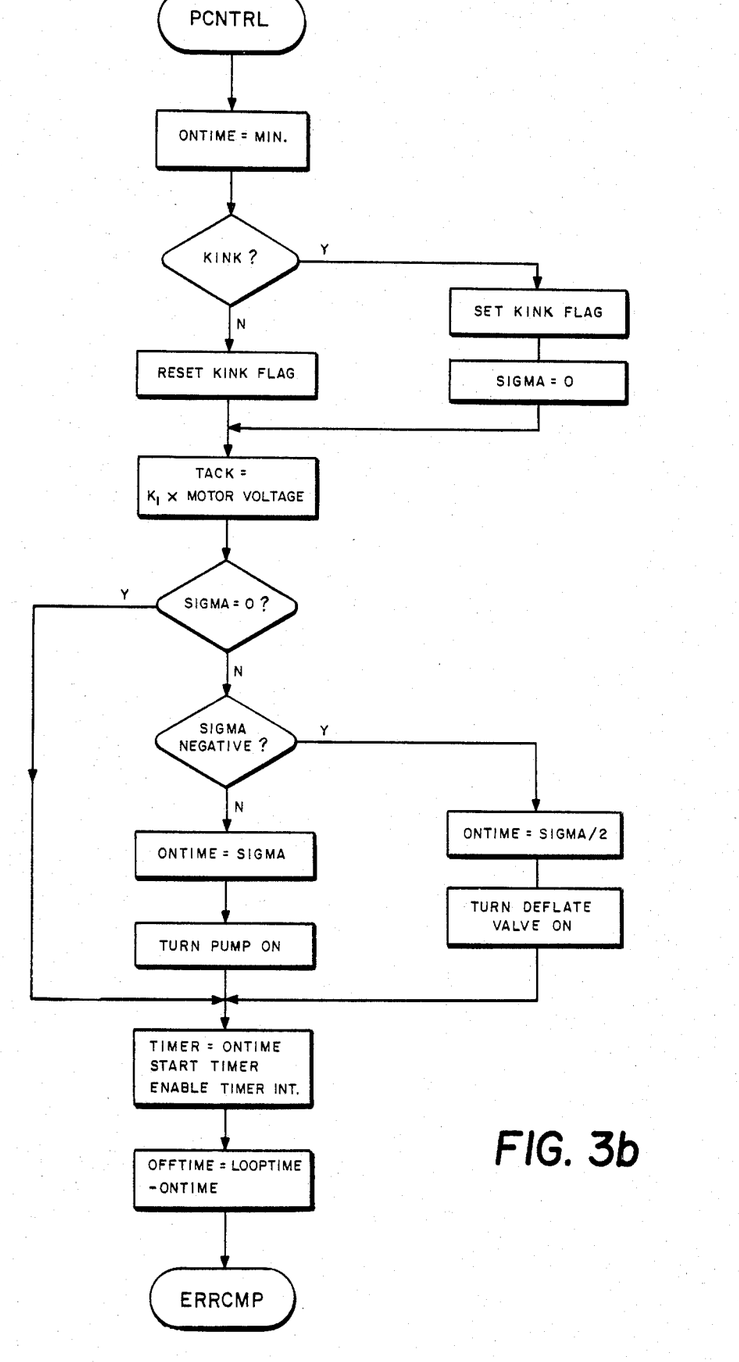

The PCNTRL program first sets the intermediate valuable ONTIME to a low nominal value. It then checks the T1 signal (microprocessor input line 19) to determine if there is a blockage in the tourniquet fluid system. If there is a blockage, the KINK flag is set for subsequent processing in another sub-program, and the value of SIGMA is forced to zero to prevent activities of the pump 21 or valve 20. If there is no blockage, the KINK flag is cleared and the value of SIGMA calculated on the previous loop (see below) is left unaltered. The program then tests for SIGMA equal to zero. If it is, then control bypasses turning the pump 21 or valve 20 on and ONTIME remains at the nominally low value set earlier. If SIGMA is not zero and is negative, then ONTIME is made equal to one-half of the absolute value of SIGMA, and the deflate valve 20 is opened. Otherwise, SIGMA is assumed to be positive and non-zero, indicating the need to supply fluid to the cuff. In this case ONTIME is made equal to SIGMA, and the pump 21 is turned on.

At this point any necessary pump or valve activity has been initiated and ONTIME has been determined. The internal time is loaded with the value of ONTIME, started, and its interrupt enabled. At the end of the PCNTRL program, program control passes to the ERRCMP program.

The timer will generate an interrupt when the programmed period has elapsed. This programmed period will be 265 microseconds times the number (ONTIME) the timer is loaded with, since the 8022 microprocessor increments its values every 265 microseconds. This time, $T_{pw}$, will be equal to MIN X 265 microseconds=265 microseconds if a kink was detected (see above), SIGMA X 265 microseconds if the motor 19 is to be turned on, or $-(SIGMA/2) \times 265$ microseconds if the valve 20 is turned on. The interrupt causes normal program execution to cease temporarily and the timer interrupt (TMRINT) routine (FIG. 3c) to be executed. This routine will turn off both the motor/pump 19/21 and deflate valve 20, disable the timer interrupt and restart the timer with a value OFFTIME=$T_L-T_{pw}$. Control then returns to the point in the main program at which the interrupt occurred.

Figure 3C:
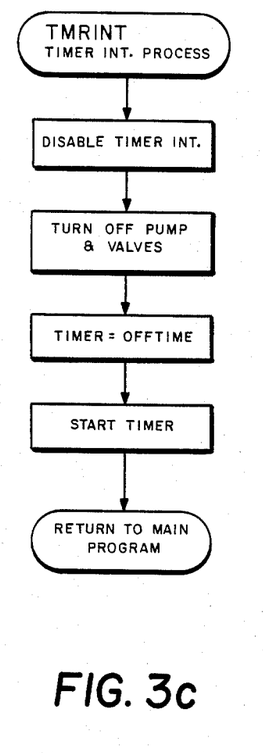

The ERRCMP program then calculates a new value for the pressure error, using the pressure provided by the PREAD program which will be discussed below. The SIGCMP program then calculates the pump/valve timing to be used in the next loop. After this timing is calculated, the program then turns to housekeeping chores which it performs while the pump is running or the valve is on. When the housekeeping errors are completed, then the system checks to see of the pump or valve is still on and if one of them is, then it continues looping until the timer interrupts.

The PREAD sub-program determines the value of the sensed pressure from the AN1 and AN0 signals input on pins 5 and 6 respectively of the microprocessor. This sub-program is shown in Fig. 3d, and can be understood from the following considerations.

Potentiometer 61 adjusts the span, that is the voltage range of pressure transducer 87. Preferably this range is adjusted so that P+ varies from 0 to AVREF as the pressure increases from 0 to the maximum scale pressure, and P— varies from AVREF to 0 as the pressure varies from the minimum to the maximum scale pressure. The balance between amplifiers 100 and 102 is then adjusted with "Zero" potentiometer 105 so that the voltages P+ and P— cross, i.e. are equal, at one-half full scale. Finally common mode potentiometers 106 is adjusted to raise the voltage P+ ¼ bit above the half-scale point and P— ¼ bit below the half-scale point. This latter adjustment is important in obtaining the increased resolution of the invention and will be discussed in more detail below.

With the voltages adjusted as described, the analog to digital converter within microprocesser 16 will move through its full 8 bits as the pressure goes from 0 to full scale. For purposes of illustration, assume that this full scale pressure is 512 mmHg. Each 1 bit increase in output from the A/D converter will then be equivalent to an increase in pressure in 2 mmHg. By considering column (c) in FIG. 5 it will be seen that if P+ is added to the inverse of P—, and the offset between these scales is considered, the $(P+)+(-P-)$ will be equal to the pressure. In order to compensate for possible errors or drift in the system which might cause the "0" level of the scale to move, the signal at zero pressure is subtracted from the signal at the given pressure to find the corrected pressure. This may be written mathematically as $P=(AN1_p-AN1_0)+(AN0_o-AN0_p)$. The term in the last parenthesis is clearly the complement of P—. This equation may be rewritten as $P=AN1_p-AN0_p+AN0_o-AN1_o$ or $P=AN1_p=AN0_p+POFSET$, where POFSET=$AN0_o-AN1_o$.

Figure 3D:
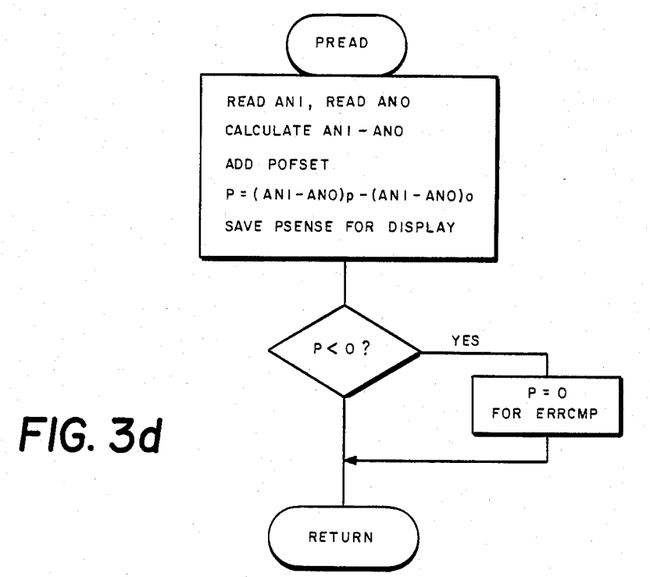
Figure 3E:
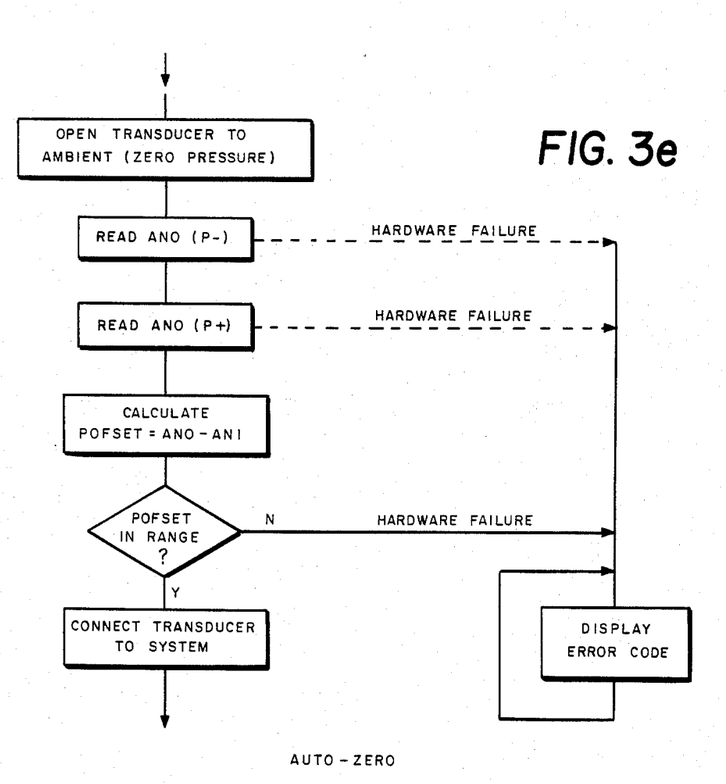

From the above, the programs given in FIGS. 3d and 3e can be understood. When the tourniquet is turned on, long-term zero drift is corrected by means of the AUTO-ZERO program given in FIG. 3d. Transducer 87 is opened to atmosphere by venting valve 25, the microprocessor reads the value of signal AN0 and the value of signal AN1, and then takes their difference. If this error is above a certain limit, then the program declares that the error is too large and displays an error code which tells the user that the pressure transducer must be recalibrated. If the error is within limits, it is saved as POFSET in memory and the transducer 87 is reconnected to the system by sense valve 25.

The PREAD program supplies the main program with current pressure measurements. First AN1 and AN0 are read, the differences taken, and POFSET is added to find the pressure. This value is saved in the microprocesor memory for subsequent processing. If the sensed pressure is less than zero, then the pressure is set equal to zero for purposes of the ERRCMP program and otherwise the valve of P calculated as given is returned to the ERRCMP program to determine the pressure adjustmemt to be made.

In the preferred embodiment, the pressure range is nominally set at —6 mmHG to 500 mmHG and the one-half scale cross-over point is 247 mmHG. This allows a little adjustment at the bottom and top of the scale for correcting for zero pressure errors. The unused quanta at the top and bottom of the 512 unit scale are used to detect circuitry and conversion errors.

It is a feature of the invention that while only an 8-bit analog-to-digital converter and associated circuitry, including the microprocessor circuitry, is used, a full pressure scale 512 mmHg range resolved in 1 mmHg steps may be obtained. This may be understood most clearly by considering column (c) in FIG. 5. It is seen that as —P— and P+ rise from 0 along the digital scale, that the one-half bit voltage offset between the two scales will cause —P— to change to 1 prior to P+. The sum of the two then gives a pressure of 1 mmHg. Then P+ changes at a pressure and voltage one-half bit higher and the sum is equal to 2, and so on up to the full 255 limit of both scales (Counting "0" as a number, 256 total numbers are available.)

Figure 5:
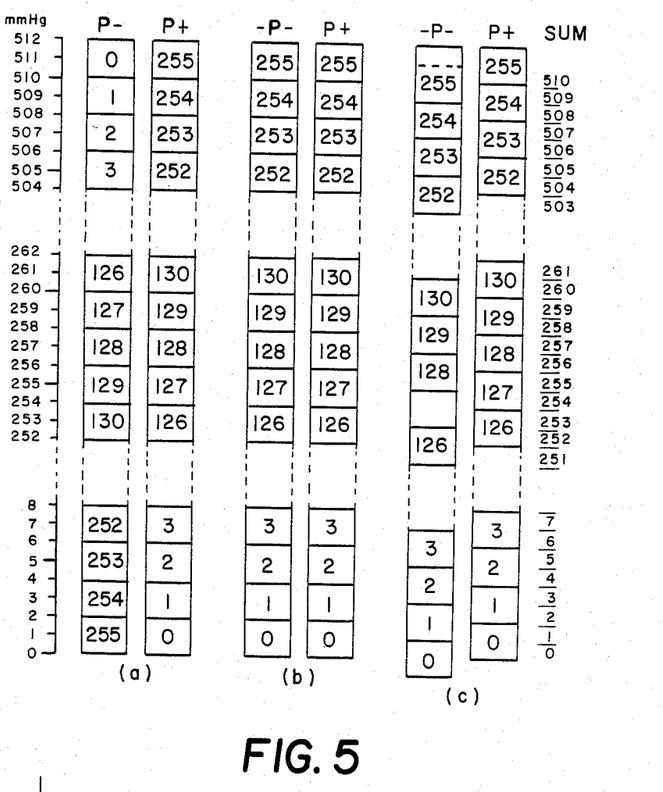
FIG. 5 is a diagrammatic illustration of the manner in which the quantized pressure signals from the positive and negatively varying sides of a pressure transducer are offset and summed by the invention to yield an increased resolution.

It is a further feature of the invention that not only is increased resolution obtainable, but this is done in a much simpler manner. For example, column A shows one scheme that may be used for obtaining a digital pressure scale. When P— is equal to 255 and P+ is equal to 0, then the pressure can be considered to be 1 mmHg, when P— is equal to 254 and P+ is equal 1, the the pressure can be considered equal to 3 mmHg. This scale has an inherent resolution of 2 mmHg. If P— is complemented and added to P+, then the determination of the pressure becomes much simpler. —P— only has to be added to P+ in order to determine the pressure; that is when —P— and P+ are 0 then the pressure is considered to be 0, when they are both 1, then the pressure is considered to be equal to 2 mmHg etc. This scale also has a resolution of 2 mmHg. The offset scale (c) not only permits the simple addition of the two values to arrive at the pressure, but also yields a resolution of 1 mmHg.

The pressure saved by the microprocessor in the PREAD program is read out of the microprocessor in a conventional fashion with the circuitry shown in FIG. 2b and described above. In the circuitry shown, the anode drive, supplied to pins 3 and 8 of each digit I4 through I10 by the scan circuitry of driver 72, is about 200 mA per digit at a duty cycle of 12%. The display scan rate is approximately 250 Hz. The LED driver 72 also includes data memory and decoding for BCD, minus sign, blanking and a HELP display. The CODE input of driver 72 pin 9, must float for proper decoding. The data locations are selected via the address inputs; A0, A1, and A2. The display data is presented on inputs D0 and D3. Strobing the /WR line low, when the address and data are firm, writes the data into memory. The only decimal point illuminated is the I5 display. This display becomes the units digit when reading battery charger voltage in the calibration mode of the tourniquet. If the DP input on driver 72 is low when writing to data location five, the decimal point will appear in the tens position of the PRESSURE display (I4 through I7).

Figure 4:
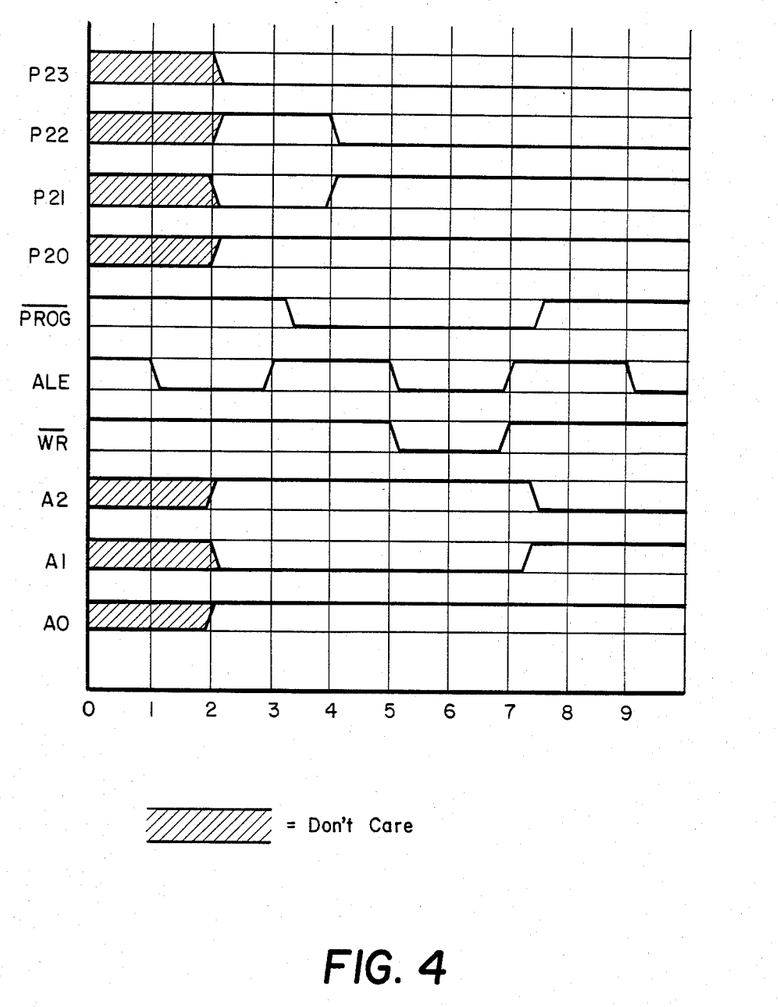
FIG. 4 is a timing diagram illustrating the timing of the signals sensed by or developed at various points in the electronic circuitry of FIGS. 2a and 2b during the writing of a digit in the display in the preferred embodiment of the invention.

As an aid to understanding the operation of the digital display circuit, an example of writing a 3, followed by a decimal point, into the PRESSURE display tens digit (I5) is illustrated by FIG. 4 and the following text. The address for this digit is a binary 101. The binary data is 0011 and the /DP input (pin 7 of driver 72) must be low when /WR goes low. The address is first set up on the P20 through P23 outputs of microprocessor 16. The address and decimal point signals are latched to the Q0, Q1, and Q3 outputs of latch 130 when /PROG goes low. Next the data is set up on P20 through P23 and is transferred to the memory of driver 72 while /WR is low. The next refresh cycle to anode 5 (AN5) updates the display digit to "3."

As mentioned above, the offsetting of the common mode voltages of amplifiers 100 and 102 by potentiometer 106 is in important feature of the invention. Another feature of the invention is that the exact AVREF voltage does not need to be known to set this potentiometer.

Figure 3F:
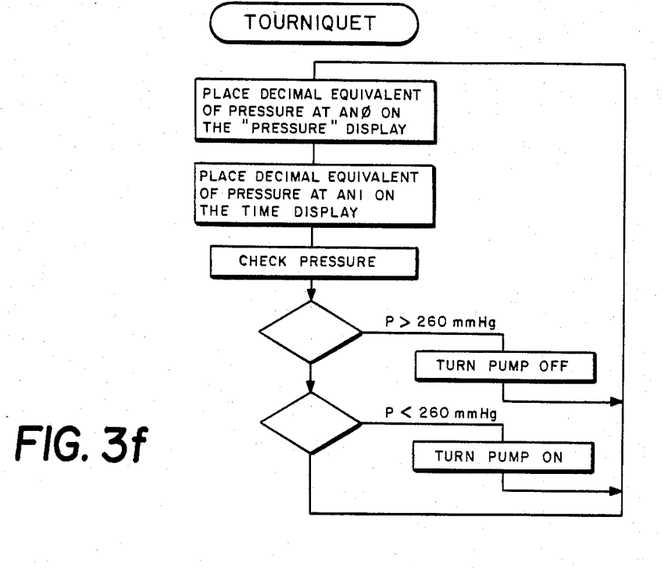
Figure 3G:
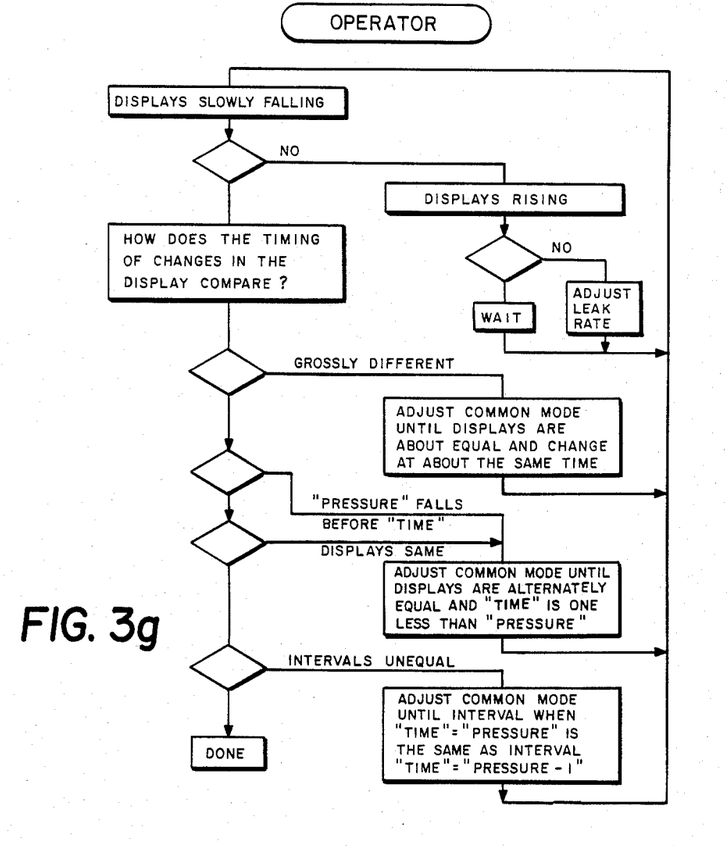
FIG. 3g is a flow-chart showing the sequence of operations to offset the digital signals according to the invention.
Figure 6:
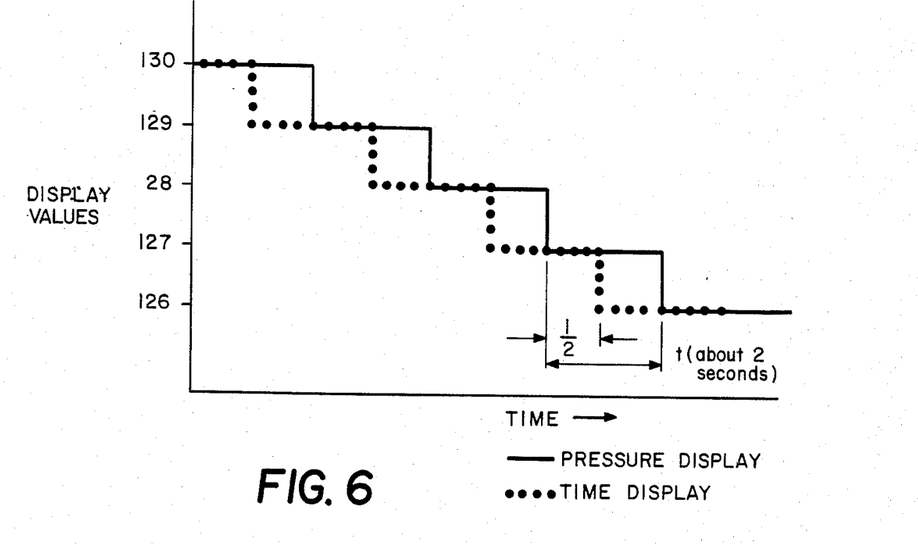
FIG. 6 shows a diagram of time versus display values that indicate that the voltage offset in a tourniquet according to the invention is correct.

FIGS. 3f and 3g show flow charts of a program that is used in the calibration mode of the tourniquet to enable this calibration to be done quickly and easily. FIG. 3f is the flow chart of tourniquet operation which proceeds simultaneously with the human operation. FIG. 3g is a "human" flow chart; that is, it shows the actions of the operation in performing the calibration. The microprocessor in the FIG. 3e program simply inverts the output of the A/D converter in microprocessor 16 corresponding to the signal AN0 and places it on the pressure display, I4 through I7. It also reads the AN1 signal and places it directly onto the time display, I8 through I10. A manometer, cuff or other pressure accumulator is connected to couplings 23A and 23B (FIG. 1) by the operator. The microprocessor calibration program pressurizes the manometer or cuff up to about 260 mmHg. A small leak is then put in the system by the operator, for example by the use of a small leak control valve. Both of the readings of the display will then fall slowly. If the two readings are observed closely the "time" display will appear to lead "pressure" display by about 50%. That is, as the pressure slowly falls, the time interval that the time display reads one less than the pressure display is equal to the time inverval over which they are the same. Potentiometer 106 is adjusted until the time display leads the pressure display by exactly 50%. The offset between the two digital signals will then be at a pressure and voltage corresponding to one-half a digital quanta. FIG. 6 shows the correct change in time and pressure displays for a leak rate of about 1 mmHg per second.

A novel tourniquet system that provides improved resolution using relatively inexpensive and simple components, and having numerous other features and advantages has been described. While the above description of the invention has been referenced to a particular embodiment, it is evident that, now that the advantages of using a plurality of offset digital pressure signals has been disclosed, those skilled in the art can now make numerous uses of, modifications of, and departures from the specific embodiments described herein without departing from the inventive concepts. For example, instead of using a differential amplifier, as the present system uses, other types of amplification systems may be used, and it is likely that these amplification systems would incorporate a different algorithm for calculating the sensed pressure. Or many different features or functions could be added or subtracted from the embodiment of the tourniquet shown. Or, many different equivalent electronic circuits may be used, which may incorporate different combinations and/or arrangements of the components described herein, or other equivalent components. Consequently, the invention is to be construed as embracing each and every novel feature and novel combination of features within the appended claims.

What we claim is:

1. A pneumatic tourniquet comprising:
   means for inflating and deflating a cuff;
   pressure sensing means for sensing the pressure in said cuff and for producing a plurality of digital signals, each signal representative of said pressure and each signal having a pressure-to-digital signal scale such that the pressures at which the transistions between digital quanta occur are different for each signal; and
   display means responsive to said plurality of signals for producing a pressure display having greater resolution than each of said digital signals.

2. A pneumatic tourniquet as in claim 1 wherein there are two of said digital signals, and wherein the transition pressures on the pressure-to-digital signal scale for one signal differ from the transistion pressures on the pressure to digital signal scale for the other signal by a pressure equal to approximately one-half a digital quantum.

3. A pneumatic tourniquet as in claim 1 wherein said pressure sensing means further comprises a means for adjusting the pressures at which the transistions between contiguous quanta occur for one of the digital signals realtive to the pressures at which the transistions between contiguous quanta occur for the other of the digital signals.

4. A pneuamtic tourniquet as in claim 1 wherein each of said digital signals is an 8-bit signal and said pressure display has a resolution corresponding to 9-bits.

5. A pneumatic tourniquet as in claim 4 wherein said pressure display is in mmHg with a resolution of 1 mmHg.

6. A pneumatic tourniquet as in claim 1 wherein said pressure sensing means comprises:
- a transducer means for producing a plurality of analog pressure signals; and
- means for converting said analog signals to digital signals.

7. A pneumatic tourniquet as in claim 6 wherein said means for converting includes a multiplexing means, and an analog-to-digital converter having an analog input and a digital output.

8. A pneumatic tourniquet as in claim 7 wherein said display includes:
- means for storing said signals; and
- means for reading the signal at said output of said analog-to-digital converter at prescribed times and storing said signals in portions of said storage means corresponding to said prescribed times; and,
- wherein said multiplexer comprises a means for applying each of said plurality of signals to said input of said analog-to-digital converter at one of said prescribed times 9. A pneumatic tourniquet as in claim 6 wherein said analog pressure signals are electrical voltage signals, and wherein said means for producing said signals comprises a means for adjusting the relative voltage levels of said signals.

10. A pneumatic tourniquet as in claim 9 wherein said means for adjusting comprises:
- means for adjusting said voltages to be substantially equal at a selected pressure; and
- means for offsetting said voltages with respect to each other.

11. A pneumatic tourniquet as in claim 10 wherein:
- said pressure is selected to be the pressure corresponding to substantially one half of the full scale pressure of said pressure transducer means; and
- said signals are offset by raising said first signal and lowering said second signal by a voltage corresponding to substantially one-fourth of a digital quantum.

12. A pneumatic tourniquet as in claim 11 wherein said means for producing a pressure display comprises a means responsive to said voltage signals for producing an output signal representative of the combination of the two signals.

13. A pneumatic tourniquet as in claim 1 and further comprising means for correcting said signals for system errors.

14. A pneumatic tourniquet as in claim 13 wherein said means for correcting comprises:
- means for storing the signals produced at a predetermined pressure value; and
- means communicating with the said means for storing for adjusting said signals by an amount related to said stored signals.

15. A pneumatic tourniquet as in claim 14 wherein said predetermined pressure is substantially zero pressure.

* * * * *